United States Patent [19]

Descamps et al.

[11] 4,117,151
[45] Sep. 26, 1978

[54] THERAPEUTIC SULFONAMIDES

[75] Inventors: Marcel Descamps, Rosieres; Charles Goldenberg, Brussels, both of Belgium

[73] Assignee: Labaz, Paris, France

[21] Appl. No.: 773,615

[22] Filed: Mar. 2, 1977

[30] Foreign Application Priority Data

Mar. 8, 1976 [GB] United Kingdom ............ 09253/76

[51] Int. Cl.$^2$ .................... C07D 307/81; A61K 31/34
[52] U.S. Cl. .................... 424/285; 424/250; 424/263; 424/267; 424/275; 260/293.57; 260/293.58; 260/294.8 C; 260/330.5; 260/346.73; 544/376; 544/364
[58] Field of Search .............. 260/346.2 R, 330.5, 260/294.8 C, 293.57, 293.58, 268 BC; 424/285, 263, 267, 250, 275

[56] References Cited

PUBLICATIONS

Johnson et al., J.A.C.S., vol. 36, pp. 372–380 (1914).

Primary Examiner—Henry R. Jiles
Assistant Examiner—Bernard Dentz
Attorney, Agent, or Firm—Mason, Kolehmainen, Rathburn & Wyss

[57] ABSTRACT

The present invention is concerned with novel sulfonamide compounds of the general formula:

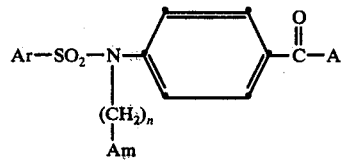

and pharmaceutically acceptable acid addition salts thereof, wherein Ar represents an optionally substituted phenyl group or a saturated heterocyclic group, Am represents a dialkylamino group or a saturated heterocyclic group, A represents a 3-benzofuryl or 3-benzo[b]thienyl group, substituted in the 2-position by a lower alkyl group and optionally substituted in the 5-position by a halogen atom or a lower alkoxy group, and n is the integer 2 or 3.

Said compounds are effective for treating certain pathological or otherwise abnormal conditions of the heart and more particularly angina pectoris.

10 Claims, No Drawings

THERAPEUTIC SULFONAMIDES

This invention relates to heterocyclic compounds and is concerned with novel substituted sulfonamide compounds and pharmaceutical compositions containing the same, and with a process for preparing the substituted sulfonamide compounds.

The substituted sulfonamide compounds with which the present invention is concerned are the compounds represented by the general formula:

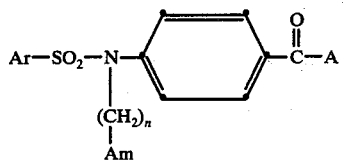

and the pharmaceutically acceptable acid addition salts thereof, wherein Ar represents an unsubstituted phenyl group, a substituted phenyl group such as p-chlorophenyl, p-methylphenyl, p-methoxyphenyl, or p-nitrophenyl, or a heterocyclic group such as a pyridyl group; Am represents a dialkylamino group such as a dimethylamino, diethylamino, di-n-propylamino or di-n-butylamino group, or a saturated heterocyclic group such as a piperidino or 4-methyl-piperazino group; A represents a 3-benzofuryl or 3-benzo [b] thienyl group, substituted in the 2-position by a branched- or straight-chain alkyl group containing from 1 to 4 carbon atoms and optionally substituted in the 5-position by a halogen atom or a lower alkoxy group such as a methoxy group, and $n$ is the integer 2 or 3.

The substituted sulfonamide of formula I can be prepared by condensing in an alkaline medium an appropriately substituted sulfonamide represented by the general formula:

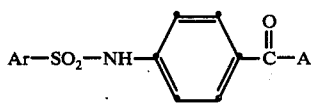

in which Ar and A have the same meanings as in formula I, with a halogenated alkylamine of the general formula:

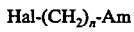

in which Am and $n$ have the same meanings as in formula I and Hal represents a halogen atom, for example chlorine, to form the required substituted sulfonamide compound of formula I, which, if desired, can be reacted with an appropriate acid to provide a pharmaceutically acceptable acid addition salt thereof.

The compounds of formula II may be prepared, using the FriedelCrafts reaction, by reacting an acyl chloride of the general formula:

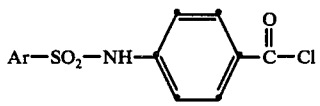

in which Ar has the same meaning as in formula I, with an appropriately substituted benzofuran or benzo [b] thiophene.

The compounds of formula IV are either known compounds, having been described by D. I. WEISBLAT, B. G. MARGELEIN, A. P. HANZE, D. R. MYERS and S. T. ROLFSON in J. Am. Chem. Soc. 75, 3625 (1953), or may be prepared by well-known methods from the corresponding acids the methods of preparation of which are known, having been described by B. J. MERGELEIN and D. I. WEISBLAT in J. Am. Chem. Soc. 76, 1702 (1954), H. K. HALL Jr. in J. Am. Chem. Soc. 78, 2570 (1956) or by F. E. REINHART in J. Franklin Inst. 236, 316 (1943).

The appropriately substituted benzofurans and benzo [b] thiophenes which are reacted with the compounds of formula IV, are known compounds, having been described by A. ARESCHKA et al. in Ind. Chim. Belg. 37, 89 (1972), M. BISAGNI, N. P. BUU-HOI and R. ROYER in J. Chem. Soc. 3688 (1955), C. HANSCH and A. BLONDON in J. Am. Chem. Soc. 70, 1561 (1948) and by N. KUCHARCZYK and V. HORAK in Coll. Czech. Chem. Comm. 33, 92 (1968), or may be prepared by methods analogous to those described in the aforesaid references.

The substituted sulfonamide compounds of the invention have been found to possess pharmacological properties likely to render them of value in the treatment of pathological conditions of the heart. In particular, compounds within the scope of the invention have been found to possess properties capable of rendering them extremely useful in the treatment of angina pectoris.

Thus the invention includes within its scope a method of treating pathological conditions of the heart, particularly angina pectoris, in a subject in need of such treatment, which comprises administering to the subject an effective amount of a substituted sulfonamide compound of formula I or a pharmaceutically acceptable acid addition salt thereof.

It is well known that pathological conditions of the heart are very difficult diseases to master.

This is particularly true in the case of angina pectoris, primarily because there are numerous factors which may precipitate an attack of angor.

These precipitating factors have been carefully investigated for several years and it is now possible to define their characteristics with accuracy and, as a consequence of this, it is possible to enumerate the conditions which an anti-anginal agent should fulfil in order to be effective in most cases.

According to R. CHARLIER in the Nouvelle Presse Medicale, 3, 2407–2410, 1974, an ideal anti-anginal agent should:

(1) Reduce the oxygen requirements of the myocardium,
(2) Increase the supply of oxygen to the myocardium,
(3) Possess anti-adrenergic properties and thus combat, at least partially, the tachycardia and increased arterial blood-pressure which result from stimulation of the sympathetic nervous system,
(4) Not depress the performance of the cardiac muscle with respect to its haemodynamic role. It should, in fact, be stimulated to a certain degree.

Amongst the anti-anginal agents so far used, very few possess the four qualities which, according to present medical practice, are required to combat effectively an anginal condition.

For instance, the nitrites improve the supply of oxygen to the myocardium without depressing cardiac functioning but do not reduce cardiac frequency. Coronary vasodilators, such as prenylamine, dipyridamole etc., increase the supply of oxygen to the myocardium and do not depress the cardiac function, but they do not reduce the oxygen requirements of the myocardium and do not inhibit the cardio-vascular reactions to adrenergic stimulants.

The β-blocking agents such as prapranolol, practolol etc., considerably reduce cardiac frequency and thereby diminish the oxygen requirements of the myocardium. They also exert an anti-adrenergic effect. However, they lower the supply of oxygen to the myocardium and depress cardiac functioning.

Another, more recent, agent is perhexiline maleate which combines the qualities of increasing the supply of oxygen to the myocardium and at the same time diminishing cardiac frequency and thereby reducing the oxygen requirements of the myocardium. Furthermore, perhexiline maleate does not appear to exert a depressant effect upon cardiac functioning. However, this substance does not possess any anti-adrenergic properties.

Amiodarone is a very succesful anti-anginal agent which has been clinically used for some years now and it possesses the four qualities which are at present recognized as being required to provide an effective and outstanding anti-anginal drug. However, amiodarone produces, alongside its anti-anginal action, certain side-effects which take the form of a microdeposit in the cornea and, in a few rare cases, the development of a cutaneous sensitivity to light which can lead to a slate-coloured pigmentation of the skin. Both of these side-effects are reversible either by suspending administration of the product or, in certain cases, by reducing the dosage. They imply nevertheless a constant supervision of the patient under treatment.

Moreover, amiodarone may produce, when used as a long-term medication, dysfunction of the thyroid gland and constant supervision of the patient from this point of view is also required, chiefly when a patient with a thyroid history is treated.

A series of compounds, chemically close to amiodarone, has been found to possess the four pharmacological properties which are at present considered as indicative of a potential anti-anginal action. Examples of such compounds are described in British Pat. Nos. 1,299,247, 1,357,212, 1,382,742 and 1,456,323. However, none of these compounds has been found, at least when used clinically, to be as useful as amiodarone and their study has therefore been abandoned.

This series of amiodarone-like compounds, which may be represented by the general formula:

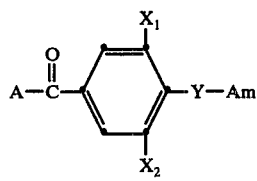

V wherein A represents a substituted 3-benzofuryl or 3-benzo[b]thienyl group, $X_1$ and $X_2$ represent a hydrogen or halogen atom or a lower alkyl radical, Y represents an oxygen atom and Am a N-substituted aminoalkyl chain, has been further developed, first by preparing compounds of general formula V wherein Y represents a —NH-group, the other substituents remaining unchanged. In spite of the well-known chemical analogy between the oxygen and nitrogen atoms, all the compounds so obtained have been found to be pharmacologically inactive.

Furthermore the compounds of general formula V wherein Y represents a

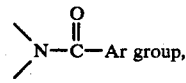

Ar representing an aryl radical, have also proved to be inactive.

Very surprisingly, the compounds of formula I, which may be considered as compounds of formula V wherein Y represents a

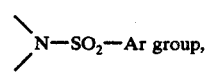

Ar representing an aryl radical, have been found to possess very useful pharmacological properties.

A first series of tests was carried out, which constitutes an initial exploration of the pharmacological possibilities of the molecules tested. These tests are also considered as a reliable guide with regard to the selection of compounds which are likely to be useful as a means of treating pathological heart conditions and in particular angina pectoris.

They number four in all and bear the references A, B, C and D.

Test A

A dose of the compound was administered intravenously to a normal dog for the purpose of reducing cardiac frequency. The reduction in cardiac frequency was noted in terms of a percentage of the initial heart-rate. In the Table given below, the degrees of reduction are expressed as follows:

| |
|---|
| 10% to 19 % = 1 |
| 20% to 29% = 2 |
| 30% to 35% = 3 |
| 36% to 40% = 4 |

Test B

The purpose of this trial was to determine the reduction in arterial blood-pressure obtained by the intravenous administration to a normal dog of a dose of the compound under study. The reduction in arterial blood-pressure was recorded as a percentage of the initial pressure. For this test, the degrees of reduction are expressed in the Table as follows:

| |
|---|
| 5% to 9% = 1 |
| 10% to 15% = 2 |
| 16% to 20% = 3 |

Test C

The purpose of this trial was to determine the percentage by which a dose of the compound under study reduced the isoprenaline-accelerated heart-rate in a dog which had previously received an intravenous dose of 1 mg/kg of atropine sulphate. The difference between the maximum accelerated heart-rate and the initial heart-rate was noted and expressed as a percentage of the latter. This percentage for purposes of convenience is referred to as X. After the effects of the isoprenaline had disappeared, a dose of the compound to be tested was administered intravenously. The animal then received the same quantity of isoprenaline as before and it was observed that the degree of maximum acceleration in cardiac frequency was less than that previously recorded. This new difference was noted and converted to a percentage of the heart-rate figure recorded before the second administration of isoprenaline. This latter percentage is referred to herein as Y. Finally, Y was subtracted from X and the result was registered as a percentage of X.

The results obtained in this test are expressed in the Table as follows:

```
20% to 29% = 1
30% to 39% = 2
40% to 44% = 3
45% to 50% = 4
```

Test D

The purpose of this trial was to determine the capacity of compounds of the invention to reduce epinephrine-increased blood-pressure in the dog which had also previously received an intravenous dose of 1 mg/kg of atropine sulphate. The same procedure was followed as in Trial C with regard to the calculation of the percentage of pressure-reduction obtained and the results are indicated in the Table in accordance with the same system.

The compounds listed hereunder were tested in the form of an acid addition salt and the results obtained are indicated in the Table below.

(1) 2-ethyl-3-[N-(3-di-n-butylaminopropyl)-N-(4-methyl-benzenesulfonyl)-4-amino-benzoyl]-benzofuran
(2) 2-ethyl-3-[N-dimethylaminoethyl)-N-(4-methoxy-benzenesulfonyl)-4-amino-benzoyl]-benzofuran
(3) 2-ethyl-3-[N-(2-diethylaminoethyl)-N-(4-methoxy-benzenesulfonyl)-4-amino-benzoyl]-benzofuran
(4) 2-ethyl-3-[N-(3-di-n-propylaminopropyl)-N-(4-methyl-benzenesulfonyl)-4-amino-benzoyl]-benzofuran
(5) 2-n-butyl-3-[N-(3-diethylaminopropyl)-N-(4-methyl-benzenesulfonyl)-4-amino-benzoyl]-benzofuran
(6) 2-n-butyl-3-[N-(3-di-n-propylaminopropyl)-N-(4-methyl-benzenesulfonyl)-4-amino-benzoyl]-benzofuran
(7) 2-n-butyl-3-[N-(2-dimethylaminoethyl)-N-(4-methyl-benzenesulfonyl)-4-amino-benzoyl]-benzofuran
(8) 2-n-propyl-3-[N-(3-di-n-propylaminopropyl)-N-(4-methyl-benzenesulfonyl)-4-amino-benzoyl]-benzofuran
(9) 2-n-propyl-3-[N-(3-di-n-butylaminopropyl)-N-(4-methyl-benzenesulfonyl)-4-amino-benzoyl]-benzofuran
(10) 2-n-butyl-3-[N-(2-dimethylaminoethyl)-N-(4-methyl-benzenesulfonyl)-4-amino-benzoyl]-benzo[b]thiophene
(11) 2-isopropyl-3-[N-(3-di-n-butylaminopropyl)-N-(4-methyl-benzenesulfonyl)-4-amino-benzoyl]-benzofuran
(12) 2-ethyl-3-[N-(2-diethylaminoethyl)-N-(4-methyl-benzenesulfonyl)-4-amino-benzoyl]-benzo[b]thiophene
(13) 2-n-butyl-3-[N-(3-di-n-propylaminopropyl)-N-(4-nitro-benzenesulfonyl)-4-amino-benzoyl]-benzofuran
(14) 2-n-butyl-3-[N-(3-di-n-butylaminopropyl)-N-(4-methoxy-benzenesulfonyl)-4-amino-benzoyl]-benzofuran The following results were obtained by using an intravenous injection of 10 mg/kg of the Compound to be tested.

TABLE I

| Compounds | Test A | Test B | Test C | Test D |
|---|---|---|---|---|
| 1 | 3 | 3 | 2 | 2 |
| 2 | 2 | 3 | 2 | 3 |
| 3 | 3 | 3 | 2 | 2 |
| 4 | 3 | 3 | 2 | 3 |
| 5 | 3 | 3 | 2 | 3 |
| 6 | 3 | 3 | 2 | 2 |
| 7 | 3 | 3 | 3 | 3 |
| 8 | 3 | 3 | 2 | 2 |
| 9 | 3 | 3 | 3 | 3 |
| 10 | 2 | 3 | 2 | 2 |
| 11 | 2 | 3 | 2 | 2 |
| 12 | 2 | 3 | 2 | 2 |
| 13 | 3 | 3 | 3 | 3 |
| 14 | 3 | 3 | 3 | 2 |

In connection with Trials A and B, it should be pointed out that the reduction figures are optimal. It is quite clear that there is a limit below which it is undesirable to go when it is a question of reducing arterial blood-pressure and cardiac frequency. Such reductions are essential, according to modern medical thinking, when it is a question of diminishing the work of the heart in order to alleviate cardiac deficiencies but, as stated above, they cannot go below a certain limit without provoking undesirable side-effects. Thus, it may be said that, for the purposes for which they are required, the above compounds have shown that they possess the necessary qualities to the most recommendable degree. Moreover, these compounds have shown (Tests C and D) that they possess anti-adrenergic properties, i.e. that they comply with the third condition which an ideal anti-anginal agent should fulfil.

Further pharmacological tests were carried out with the preferred compound of the present invention, i.e. 2-n-butyl-3-[N-(2-dimethylaminoethyl)-N-(4-methyl-benzenesulfonyl)-4-amino-benzoyl]-benzofuran (Compound No. 7) which was used in hydrochloride form, namely:

(1) The capability of Compound No. 7 of increasing the blood-flow to the myocardium and thus stepping up the supply of oxygen to this muscle was determined in accordance with the technique described by R. CHARLIER and J. BAUTHIER in Arzneimittel Forschung "Drug Research" 23, 1305–1311 (1973).

Seven experiments were carried out on seven dogs, using a intravenous injection of 10 mg/kg of Compound No. 7. Arterial coronary blood-flow was measured (ml/min) in each animal and it was found that the effect of compound No. 7 was approximately the same for all the animals, the maximal increase in blood-flow to the myocardium being about 94% after 3 minutes. The increase in blood-flow was regular and the return to the control values took place progressively within twenty minutes.

From the above test, it may be concluded that Compound No. 7 increases to a very marked degree the supply of oxygen to the myocardium and thus complies with the second condition which an ideal anti-anginal agent should fulfil.

(2) A series of tests was carried out with a view to demonstrating that Compound No. 7 does not depress the performance of the cardiac muscle.

The same experimental conditions as above were observed and the following parameters were measured:
(a) Cardiac output Increases in the cardiac output of 70% and 50% were found after 2.5 minutes and 5 minutes respectively, the return to the control value taking place progressively within 20 minutes.

(b) Cardiac frequency

The cardiac frequency dropped to a highly significant degree during 60 minutes, i.e. during the total duration of the experiment.

(c) Stroke volume

At the present time, there does not exist any established means of measuring stroke volume, but cardiac output and cardiac frequency can be measured with accuracy. Thus, in order to determine the effect of any particular substance on stroke volume, it is sufficient to divide cardiac output by the number of heart-beats per minute.

The following results were obtained from an initial value of 100%:

| Time min. | 2.5 | 5 | 10 | 15 | 20 | 25 | 30 | 35 | 40 | 45 | 50 | 55 | 60 |
|---|---|---|---|---|---|---|---|---|---|---|---|---|---|
| Stroke Volume % | 213 | 200 | 172 | 152 | 143 | 136 | 137 | 138 | 127 | 127 | 130 | 120 | 117 |

The stroke volume increases to a very marked degree (above 100%) during the first 5 minutes of the experiment, progressively decreasing later on but being always superior to the control values.

From this series of tests, it may be assumed that Compound No. 7 does not depress the performance of the cardiac muscle, and even stimulates this extremely important factor of cardiac functioning. Compound No. 7 complies therefore with the fourth condition which an ideal anti-anginal agent should fulfil.

A pharmacological test was also carried out with a view to determining whether Compound No. 7 complies with the first condition which an ideal anti-anginal agent should fulfil.

Owing to the particular importance of this test, a comparative trial was carried out with Compound No. 7 and amiodarone, which is one of the most successful anti-anginal agents used up-to-present.

This comparative trial aimed at determining the respective capabilities of the two substances to reduce the oxygen consumption of the myocardium. This property was measured by the indirect method known as the "rate-pressure product" which is a widely used and accurate haemodynamic index of myocardial oxygen consumption.

This method requires two cardiovascular parameters to be measured simultaneously, namely the mean aortic systolic blood-pressure and the heart-rate.

The "rate-pressure product" is obtained by multiplying the number of heart beats per minute by the mean aortic systolic blood-pressure. This provides an index of the total amount of oxygen used by the myocardium over a period of one minute. As it thus represents an accurate indication of the oxygen consumption of the myocardium, any lowering of the "rate-pressure product" indicates a corresponding drop in the oxygen consumption of the myocardium.

The value of this system of measurement is clearly described, for example, by B. ROBINSON in Circulation, 35, 1073 (1967).

These tests were carried out on dogs which had been previously anaesthetized with sodium pentobarbital (30 mg/kg by intravenous route).

Both Compound No. 7 and amiodarone were administered intravenously in a dose of 10 mg/kg. Compound No. 7 was administered in the form of a 2% aqueous solution of its hydrochloride salt and amiodarone in the form of a 5% aqueous solution of its hydrochloride salt. In both cases, the injection of 10 mg/kg took 2 minutes to administer.

The following results were obtained:

TABLE III

| | Oxygen Consumption | |
|---|---|---|
| Intervals of Measurement | Compound No. 7 | Amiodarone |
| Before administration of the product | 100 | 100 |
| 2.5 minutes after administration | 54.4 | 80.9 |
| 5 minutes after administration | 57.8 | 79.1 |
| 10 minutes after administration | 63.5 | 81.7 |
| 15 minutes after administration | 64.8 | 79.7 |
| 20 minutes after administration | 64.8 | 79.6 |
| 25 minutes after administration | 65.2 | 80.4 |
| 30 minutes after administration | 65.6 | 80.2 |
| 35 minutes after administration | 66.0 | 79.6 |
| 40 minutes after administration | 66.8 | 79.6 |
| 45 minutes after administration | 67.2 | 79.6 |
| 50 minutes after administration | 67.6 | 80.9 |
| 55 minutes after administration | 68.9 | 80.0 |
| 60 minutes after administration | 68.9 | 79.1 |

From the above results, it may be concluded that the preferred compound of the present invention is markedly superior to amiodarone with regard to the reduction of the oxygen consumption of the myocardium.

Finally, acute toxicity tests were carried out on rats and mice with Compound No. 7 and on rats with Compounds Nos. 13 and 14, the animals being kept under observation for 12 days following one single administration.

The following results were obtained:

a) Compound No. 7

| Animals | Administration | $LD_0$ mg/kg | $LD_{50}$ mg/kg | $LD_{95}$ mg/kg |
|---|---|---|---|---|
| Rats | intraperitoneal | 160 | 600 | 1400 |
|  | intragastric | 800 | 1600 | 2400 |
| Mice | intraperitoneal | 50 | 275 | 900 |
|  | intragastric | 550 | 2100 | 5000 | b) Compound No. 13

| Animal | Administration | $LD_0$ mg/kg | $LD_{50}$ mg/kg | $LD_{95}$ mg/kg |
|---|---|---|---|---|
| Rat | intraperitoneal | 180 | 1000 | 3000 | c) Compound No. 14

| Animal | Administration | $LD_0$ mg/kg | $LD_{50}$ mg/kg | $LD_{95}$ mg/kg |
|---|---|---|---|---|
| Rat | intraperitoneal | 200 | 1000 | 3000 |

The above pharmacological study has shown that Compound No. 7 complies with the four conditions which an anti-anginal agent should fulfil and that this compound may be assumed to be of considerable value in the treatment of pathological conditions of the heart.

Moreover, the toxicity values compare very favourably with the active dose (10 mg/kg) of which the effects are described above and show that there is a very wide safety margin between the toxic doses and the therapeutic dose of the preferred compound of the invention.

It will be appreciated that, for therapeutic use, the compounds of the invention will normally be administered in the form of a pharmaceutical composition containing, as active principle, at least one compound of formula I or a pharmaceutically acceptable acid addition salt thereof in association with a pharmaceutical carrier or excipient therefor.

Advantageously, for clinical use the composition will be made up in a dosage unit form appropriate to the desired mode of administration, for example a coated or uncoated tablet or a hard- or soft-gelatin capsule for oral administration, a solution for injection or a suppository for rectal administration.

Irrespective of the form which the composition takes, the pharmaceutical composition will normally comprise at least one of the compounds of formula I or a pharmaceutically acceptable acid addition salt thereof associated with an appropriate pharmaceutical diluent or excipient comprising, for example, one or more of the following substances: milk-sugar, starches, talc, magnesium stearate, polyvinylpyrrolidone, alginic acid, colloidal silica or a flavouring agent.

The following Examples illustrate the invention:

EXAMPLE 1

2-n-Butyl-3-[N-(2-dimethylaminoethyl)-N-(4-methyl-benzenesulfonyl)-4-amino-benzoyl]-benzofuran hydrochloride

(a) Preparation of 2-n-butyl-3-[N-(4-methyl-benzenesulfonyl)-4-aminobenzoyl]-benzofuran In a one-liter flask fitted with a mechanical stirrer and a droppingfunnel 26 g. (0.15 mol) of 2-n-butyl-benzofuran and 54 g. (0.175 mol) of N-(4-methyl-benzenesulfonyl)-4-amino-benzoyl chloride were dissolved in 600 ml. of anhydrous 1,2-dichlorethane.

At room-temperature 33 ml. (0.28 mol) of tin tetrachloride were added and the reaction medium was stirred at room-temperature for 90 minutes. To the solution so formed were then progressively added 500 ml. of water and the resulting aqueous and organic phases were separated by decantation. The organic phase was washed twice with 500 ml. of water and dried over anhydrous calcium sulphate.

The solvent was evaporated off and the residue was recrystallized from isopropanol to give 35 g. of 2-n-butyl-3-[N-(4-methyl-benzenesulfonyl)-4-amino-benzoyl]-benzofuran.

Yield: 55% M.P.: 154° C.

By the procedure described above and using the appropriate starting products, the compounds listed hereunder were prepared:

| Compound | Melting Point ° C. |
| --- | --- |
| 2-methyl-3-(N-benzenesulfonyl-4-amino-benzoyl)-benzofuran | 135 (isopropanol) |
| 2-methyl-3-[N-(4-methyl-benzenesulfonyl)-4-amino-benzoyl]-benzofuran | 162 (isopropanol) |
| 2-ethyl-3-(N-benzenesulfonyl-4-amino-benzoyl)-benzofuran | 157 (isopropanol) |
| 2-ethyl-3-[N-(4-chloro-benzenesulfonyl)-4-amino-benzoyl]-benzofuran | 137–139 (methanol) |
| 2-ethyl-3-[N-(4-methyl-benzenesulfonyl)-4-amino-benzoyl]-benzofuran | 182–184 (ethanol) |
| 2-ethyl-3-[N-(4-methoxy-benzenesulfonyl)-4-amino-benzoyl]-benzofuran | 163–166 (ethanol) |
| 5-chloro-2-ethyl-3-[N-(4-methyl-benzenesulfonyl)-4-amino-benzoyl]-benzofuran | 174 (isopropanol) |
| 2-n-propyl-3-[N-(4-methyl-benzenesulfonyl)-4-amino-benzoyl]-benzofuran | 163–165 (isopropanol) |
| 2-isopropyl-3-[N-(4-methyl-benzenesulfonyl)-4-amino-benzoyl]-benzofuran | 155–157 (isopropanol) |
| 2-n-butyl-3-(N-benzenesulfonyl-4-amino-benzoyl)-benzofuran | 128 (isopropanol) |
| 2-n-butyl-3-[N-(4-methoxy-benzenesulfonyl)-4-amino-benzoyl]-benzofuran | 132 (isopropanol) |
| 2-n-butyl-3-[N-(4-nitro-benzenesulfonyl)-4-amino-benzoyl]-benzofuran | 167–171 (isopropanol) |

(b) Preparation of 2-n-butyl-3-[N-(2-dimethylaminoethyl)-N-(4-methyl-benzenesulfonyl)-4-amino-benzoyl]-benzofuran hydrochloride In a two-liter flask equipped with a mechanical stirrer and a condenser were introduced 44.7 g (0.1 mol) of 2-n-butyl-3-[N-(4-methyl-benzenesulfonyl)-4-amino-benzoyl]-benzofuran, 60 g (0.45 mol) of potassium carbonate and 800 ml of 1,2-dichlorethane containing 15 ml of water.

While stirring the mixture was refluxed for three and a half hours, after which 14.4 g (0.1 mol) of 1-chloro-2-dimethylaminoethane hydrochloride were added and the reaction medium was again refluxed for six hours. The solvent was evaporated off under reduced vacuum and the residue was taken up in ether, washed three times with water and dried over anhydrous calcium sulphate.

By adding a saturated solution of hydrochloric acid in anhydrous ether the hydrochloride was obtained which was recrystallized from 600 ml of ethyl acetate completely dissolved in boiling methanol to give 28.6 g of 2-n-butyl-3-[N-(2-dimethylaminoethyl-N-(4-methyl-benzenesulfonyl)-4-amino-benzoyl]-benzofuran hydrochloride.

Yield: 51%. M.P.: 198° C.

Following the procedure described above and using the appropriate starting products, the compounds listed hereunder were prepared:

| Compounds | Melting Point ° C. |
| --- | --- |
| 2-methyl-3-[N-(2-dimethylaminoethyl)-N-benzenesulfonyl-4-amino-benzoyl]-benzofuran acid oxalate | 134 (ethyl acetate/isopropanol) |
| 2-methyl-3-[N-(2-diethylaminoethyl)-N-benzenesulfonyl-4-amino-benzoyl]-benzofuran acid oxalate | 150 (ethyl acetate) |
| 2-methyl-3-[N-(3-dimethylaminopropyl)-N-benzenesulfonyl-4-amino-benzoyl]-benzofuran acid oxalate | 95 (ethyl acetate) |
| 2-methyl-3-[N-(3-diethylaminopropyl)-N-benzenesulfonyl-4-amino-benzoyl]-benzofuran acid oxalate | 93 (ethyl acetate) |
| 2-methyl-3-[N-(3-di-n-propylaminopropyl)-N-benzenesulfonyl-4-amino-benzoyl]-benzofuran acid oxalate | 80 (isopropanol) |
| 2-methyl-3-[N-(3-di-n-butylaminopropyl)-N-benzenesulfonyl-4-amino-benzoyl]-benzofuran acid oxalate | 106 (ethyl acetate) |
| 2-methyl-3-[N-(2-dimethylaminoethyl)-N-(4-methyl-benzenesulfonyl)-4-amino-benzoyl]-benzofuran hydrochloride | 203–205 (isopropanol) |
| 2-methyl-3-[N-(2-diethylaminoethyl)-N-(4- | 140 |

-continued

| Compounds | Melting Point °C |
|---|---|
| methyl-benzenesulfonyl)-4-amino-benzoyl]benzofuran acid oxalate | (ethyl acetate) |
| 2-methyl-3-[N-(3-dimethylaminopropyl)-N-(4-methyl-benzenesulfonyl)-4-amino-benzoyl]benzofuran acid oxalate | 118–120 (ethyl acetate) |
| 2-methyl-3-(N-(3-diethylaminopropyl)-N-(4-methyl-benzenesulfonyl)-4-amino-benzoyl]benzofuran acid oxalate | 149 (ethyl acetate/isopropanol) |
| 2-methyl-3-[N-(3-di-n-propylaminopropyl)-N-(4-methyl-benzenesulfonyl)-4-amino-benzoyl]-benzofuran sesquioxalate | 144–150 (ethyl acetate) |
| 2-methyl-3-[N-(3-di-n-butylaminopropyl)-N-(4-methyl-benzenesulfonyl)-4-amino-benzoyl]-benzofuran acid oxalate | 112 (ethyl acetate) |
| 2-ethyl-3-[N-(2-dimethylaminoethyl)-N-benzenesulfonyl-4-amino-benzoyl]-benzofuran hydrochloride | 133 (ethyl acetate/isopropanol) |
| 2-ethyl-3-[N-(2-diethylaminoethyl)-N-benzenesulfonyl-4-amino-benzoyl]-benzofuran hydrochloride | 146 (ethyl acetate/isopropanol) |
| 2-ethyl-3-[N-(3-dimethylaminopropyl)-N-benzenesulfonyl-4-amino-benzoyl]-benzofuran hydrochloride | 143 (isopropanol) |
| 2-ethyl-3-[N-(3-diethylaminopropyl)-N-benzenesulfonyl-4-amino-benzoyl]-benzofuran hydrochloride | 92 (ethyl acetate) |
| 2-ethyl-3-[N-(3-di-n-propylaminopropyl)-N-benzenesulfonyl-4-amino-benzoyl]-benzofuran sesquioxalate | 123 (ethyl acetate) |
| 2-ethyl-3-[N-(3-di-n-butylaminopropyl)-N-benzenesulfonyl-4-amino-benzoyl]-benzofuran acid oxalate | 181 (ethyl acetate) |
| 2-ethyl-3-[N-(2-dimethylaminoethyl)-N-(4-chloro-benzenesulfonyl)-4-amino-benzoyl]-benzofuran hydrochloride | 217–223 (ethyl acetate/methanol) |
| 2-ethyl-3-[N-(2-chloro-benzenesulfonyl)-4-amino-benzoyl]-benzofuran hydrochloride | 151–156 (ethyl acetate) |
| 2-ethyl-3-[N-(3-dimethylaminopropyl)-N-(4-chloro-benzenesulfonyl)-4-amino-benzoyl]-benzofuran hydrochloride | 180–188 (ethyl acetate/methanol) |
| 2-ethyl-3-[N-(3-diethylaminopropyl)-N-(4-chloro-benzenesulfonyl)-4-amino-benzoyl]-benzofuran hydrochloride | 103–107 (ethyl acetate) |
| 2-ethyl-3-[N-(3-di-n-propylaminopropyl)-N-(4-chloro-benzenesulfonyl)-4-amino-benzoyl]-benzofuran hydrochloride | 130–134 (ethyl acetate) |
| 2-ethyl-3-[N-(3-di-n-butylaminopropyl)-N-(4-chloro-benzenesulfonyl)-4-amino-benzoyl]-benzofuran acid oxalate | 119–121 (ethyl acetate) |
| 2-ethyl-3-[N-(2-dimethylaminoethyl-N-(4-methyl-benzenesulfonyl)-4-amino-benzoyl]-benzofuran acid oxalate | 152–158 (isopropanol) |
| 2-ethyl-3-[N-(2-diethylaminoethyl)-N-(4-methyl-benzenesulfonyl)-4-amino-benzoyl]-benzofuran acid oxalate | 147–150.5 (isopropanol) |
| 2-ethyl-3-[N-(2-di-n-propylaminoethyl)-N-(4-methyl-benzenesulfonyl)-4-amino-benzoyl]-benzofuran acid oxalate | 136–139 (isopropanol) |
| 2-ethyl-3-[N-(2-di-n-butylaminoethyl)-N-(4-methyl-benzenesulfonyl)-4-amino-benzoyl]-benzofuran hydrochloride | 63–67 (ether) |
| 2-ethyl-3-[N-2-(4'-methylpiperazino)-ethyl-N-(4-methyl-benzenesulfonyl)-4-amino-benzoyl]-benzofuran dihydrochloride | 218–223 (methanol) |
| 2-ethyl-3-[N-(3-dimethylaminopropyl)-N-(4-methyl-benzenesulfonyl)-4-amino-benzoyl]-benzofuran acid oxalate | 149–154 (isopropanol) |
| 2-ethyl-3-[N-(3-diethylaminopropyl)-N-(4-methyl-benzenesulfonyl)-4-amino-benzoyl]-benzofuran acid oxalate | 80–83 (ethyl acetate) |
| 2-ethyl-3-[N-(3-di-n-propylaminopropyl)-N-(4-methyl-benzenesulfonyl)-4-amino-benzoyl]-benzofuran acid oxalate | 118–122 (ethyl acetate) |
| 2-ethyl-3-[N-(3-di-n-butylaminopropyl)-N-(4-methyl-benzenesulfonyl)-4-amino-benzoyl]-benzofuran acid oxalate | 90–101 (ethyl acetate) |
| 2-ethyl-3-[N-(3-piperidinopropyl)-N-(4-methyl-benzenesulfonyl)-4-amino-benzoyl]-benzofuran acid oxalate | 97–99 (ethyl acetate) |
| 2-ethyl-3-[N-(2-dimethylaminoethyl)-N-(4-methoxy-benzenesulfonyl)-4-amino-benzoyl]-benzofuran acid oxalate | 170–174 (isopropanol) |
| 2-ethyl-3-[N-(2-diethylaminoethyl)-N-(4-methoxy-benzenesulfonyl)-4-amino-benzoyl]-benzofuran acid oxalate | 131–133.5 (isopropanol) |
| 2-ethyl-3-[N-(3-dimethylaminopropyl)-N-(4-methoxy-benzenesulfonyl)-4-amino-benzoyl]-benzofuran acid oxalate | 150–155 (isopropanol) |
| 2-ethyl-3-[N-(3-diethylaminopropyl)-N-(4-methoxy-benzenesulfonyl)-4-amino-benzoyl]-benzofuran acid oxalate | 109–114 (ethyl acetate) |
| 2-ethyl-3-[N-(3-di-n-propylaminopropyl)-N-(4-methoxy-benzenesulfonyl)-4-amino-benzoyl]-benzofuran acid oxalate | 63–65 (ethyl acetate) |
| 2-ethyl-3-[N-(3-di-n-butylaminopropyl)-N-(4-methoxy-benzenesulfonyl)-4-amino-benzoyl]-benzofuran acid oxalate | 86–88 (isopropanol) |
| 2-ethyl-3-[N-(3-piperidinopropyl)-N-(4-methoxy-benzenesulfonyl)-4-amino-benzoyl]-benzofuran acid oxalate | 85–87 (ethyl acetate) |
| 5-chloro-2-ethyl-3-[N-(2-dimethylaminoethyl)-N-(4-methyl-benzenesulfonyl)-4-amino-benzoyl]-benzofuran hydrochloride | 231–235 (isopropanol) |
| 5-chloro-2-ethyl-3-[N-(2-diethylaminoethyl)-N-(4-methyl-benzenesulfonyl)-4-amino-benzoyl]-benzofuran hydrochloride | 110–113 (acetone/ether) |
| 5-chloro-2-ethyl-3-[N-(3-dimethylaminopropyl)-N-(4-methyl-benzenesulfonyl)-4-amino-benzoyl]-benzofuran acid oxalate | 140–143 (isopropanol) |
| 5-chloro-2-ethyl-3-[N-(3-diethylaminopropyl)-N-(4-methyl-benzenesulfonyl)-4-amino-benzoyl]-benzofuran acid oxalate | 124–125 (isopropanol) |
| 5-chloro-2-ethyl-3-[N-(3-di-n-propylaminopropyl)-N-(4-methyl-benzenesulfonyl)-4-amino-benzoyl]-benzofuran acid oxalate | 75–78 (isopropanol) |
| 5-chloro-2-ethyl-3-[N-(3-di-n-butylaminopropyl)-N-(4-methyl-benzenesulfonyl)-4-amino-benzoyl]-benzofuran acid oxalate | 78–80 (isopropanol) |
| 2-n-propyl-3-[N-(2-dimethylaminoethyl)-N-(4-methyl-benzenesulfonyl)-4-amino-benzoyl]-benzofuran hydrochloride | 207–214 (ethyl acetate/methanol) |
| 2-n-propyl-3-[N-(2-diethylaminoethyl)-N-(4-methyl-benzenesulfonyl)-4-amino-benzoyl]-benzofuran hydrochloride | 86–89 (isopropanol) |
| 2-n-propyl-3-[N-(3-dimethylaminopropyl)-N-(4-methyl-benzenesulfonyl)-4-amino-benzoyl]-benzofuran hydrochloride | 143–145 (isopropanol) |
| 2-n-propyl-3-[N-(3-diethylaminopropyl)-N-(4-methyl-benzenesulfonyl)-4-amino-benzoyl]-benzofuran hydrochloride | 133–136 (isopropanol) |
| 2-n-propyl-3-[N-(3-di-n-propylaminopropyl)-N-(4-methyl-benzenesulfonyl)-4-amino-benzoyl]-benzofuran acid oxalate | 70–77 (ethyl acetate/ether) |
| 2-n-propyl-3-[N-(3-di-n-butylaminopropyl)-N-(4-methyl-benzenesulfonyl)-4-amino-benzoyl]-benzofuran acid oxalate | 87–89 (ethyl acetate) |
| 2-isopropyl-3-[N-(2-dimethylaminoethyl)-N-(4-methyl benzenesulfonyl)-4-amino-benzoyl]-benzofuran hydrochloride | 207–210 (isopropanol) |
| 2-isopropyl-3-[N-(2-diethylaminoethyl)-N-(4-methyl-benzenesulfonyl)-4-amino-benzoyl]-benzofuran acid oxalate | 137–141 (isopropanol) |
| 2-isopropyl-3-[N-(3-dimethylaminopropyl)-N-(4-methyl-benzenesulfonyl)-4-amino-benzoyl]-benzofuran acid oxalate | 131–139 (ethyl acetate) |
| 2-isopropyl-3-[N-(3-diethylaminopropyl)-N-(4-methyl-benzenesulfonyl)-4-amino-benzoyl]-benzofuran acid oxalate | 139–143 (ethyl acetate) |
| 2-isopropyl-3-[N-(3-di-n-propylaminopropyl)-N-(4-methyl-benzenesulfonyl)-4-amino-benzoyl]-benzofuran acid oxalate | 68–70 (ethyl acetate) |
| 2-isopropyl-3-[N-(3-di-n-butylaminopropyl)-N-(4-methyl-benzenesulfonyl)-4-amino-benzoyl]-benzofuran acid oxalate | 89–91 (ethyl acetate) |
| 2-n-butyl-3-[N-(2-dimethylaminoethyl)-N-benzenesulfonyl-4-amino-benzoyl]-benzofuran hydrochloride | 119 (ethyl acetate) |
| 2-n-butyl-3-[N-(2-diethylaminoethyl)-N-benzenesulfonyl-4-amino-benzoyl]-benzofuran acid oxalate | 142 (isopropanol) |
| 2-n-butyl-3-[N-(3-dimethylaminopropyl)-N-benzenesulfonyl-4-amino-benzoyl]-benzofuran acid oxalate | 138 (ethanol) |
| 2-n-butyl-3-[N-(3-diethylaminopropyl)-N-benzenesulfonyl-4-amino-benzoyl]-benzofuran acid oxalate | 117 (ethyl acetate) |
| 2-n-butyl-3-[N-(3-di-n-propylaminopropyl)-N-benzenesulfonyl-4-amino-benzoyl]-benzofuran hydrochloride | 117 (ethyl acetate) |
| 2-n-butyl-3-[N-(3-di-n-butylaminopropyl)-N-benzenesulfonyl-4-amino-benzoyl]-benzofuran acid oxalate | 102 (ethyl acetate) |
| 2-n-butyl-3-[N-(2-diethylaminoethyl)-N-(4-methyl-benzenesulfonyl)-4-amino-benzoyl]- | 143 (ethyl |

-continued

| Compounds | Melting Point °C. |
|---|---|
| benzofuran hydrochloride | acetate) |
| 2-n-butyl-3-[N-(3-dimethylaminopropyl)-N-(4-methyl-benzenesulfonyl)-4-amino-benzoyl]-benzofuran hydrochloride | 146 (ethyl acetate) |
| 2-n-butyl-3-[N-(3-di-n-propylaminopropyl)-N-(4-methyl-benzenesulfonyl)-4-amino-benzoyl]-benzofuran hydrochloride | 127 (ethyl acetate) |
| 2-n-butyl-3-[N-(3-diethylaminopropyl)-N-(4-methyl-benzenesulfonyl)-4-amino-benzoyl]-benzofuran hydrochloride | 113 (ethyl acetate) |
| 2-n-butyl-3-[N-(3-di-n-butylaminopropyl)-N-(4-methyl-benzenesulfonyl)-4-amino-benzoyl]-benzofuran acid oxalate | 116 (ethyl acetate) |
| 2-n-butyl-3-[N-(3-piperidinopropyl)-N-(4-methyl-benzenesulfonyl)-4-amino-benzoyl]-benzofuran hydrochloride | 105 (ethyl acetate) |
| 2-n-butyl-3-[N-(2-dimethylaminoethyl)-N-(4-methoxy-benzenesulfonyl)-4-amino-benzoyl]-benzofuran hydrochloride | 172 (isopropanol) |
| 2-n-butyl-3-[N-(2-diethylaminoethyl)-N-(4-methoxy-benzenesulfonyl)-4-amino-benzoyl]-benzofuran hydrochloride | 138 (ethyl acetate) |
| 2-n-butyl-3-[N-(3-dimethylaminopropyl)-N-(4-methoxy-benzenesulfonyl)-4-amino-benzoyl]-benzofuran acid oxalate | 128 (ethyl acetate/isopropanol) |
| 2-n-butyl-3-[N-(3-diethylaminopropyl)-N-(4-methoxy-benzenesulfonyl)-4-amino-benzoyl]-benzofuran oxalate | 81–82 (ethyl acetate) |
| 2-n-butyl-3-[N-(3-di-n-propylaminopropyl)-N-(4-methoxy-benzenesulfonyl)-4-amino-benzoyl]-benzofuran acid oxalate | 80 (ethyl acetate) |
| 2-n-butyl-3-[N-(3-di-n-butylaminopropyl)-N-(4-methoxy-benzenesulfonyl)-4-amino-benzoyl]-benzofuran oxalate | 126–127 (ethyl acetate) |
| 2-n-butyl-3-[N-(2-dimethylaminoethyl)-N-(4-nitro-benzenesulfonyl)-4-amino-benzoyl]-benzofuran hydrochloride | 219–222 (isopropanol) |
| 2-n-butyl-3-[N-(2-diethylaminoethyl)-N-(4-nitro-benzenesulfonyl)-4-amino-benzoyl]-benzofuran acid oxalate | 155–158 (isopropanol) |
| 2-n-butyl-[N-(3-dimethylaminopropyl)-N-(4-nitro-benzenesulfonyl)-4-amino-benzoyl]-benzofuran hydrochloride | 176–179 (isopropanol) |
| 2-n-butyl-3-[N-(3-diethylaminopropyl)-N-(4-nitro-benzenesulfonyl)-4-amino-benzoyl]-benzofuran acid oxalate | 96–100 (ethyl acetate) |
| 2-n-butyl-3-[N-(3-di-n-propylaminopropyl)-N-(4-nitro-benzenesulfonyl)-4-amino-benzoyl]9-benzofuran acid oxalate | 73–75 (isopropanol) |
| 2-n-butyl-3-[N-(3-di-n-butylaminopropyl)-N-(4-nitro-benzenesulfonyl)-4-amino-benzoyl]-benzofuran acid oxalate | 118–122 (isopropanol) |

EXAMPLE 2

2-n-Butyl-3-[N-(2-dimethylaminoethyl)-N-(4-methyl-benzenesulfonyl)-4-amino-benzoyl]-benzo[b] thiophene hydrochloride (a) Preparation of 2-n-butyl-3-[N-(4-methyl-benzenesulfonyl)-4-aminobenzoyl]-benzo [b] thiophene Into a one-liter flask equipped with a mechanical stirrer and a dropping-funnel were dissolved 19 g (0.1 mol) of 2-n-butyl-benzo [b] thiophene and 32 g (0.105 mol) of (4-methyl-benzenesulfonyl)-4-amino-benzoyl chloride in 350 ml of 1,2-dichlorethane.

Through the dropping-funnel were rapidly added, drop-by-drop, 25 ml (0.21 mol) of tin tetrachloride and the mixture was stirred at room-temperature for one hour, after which 300 ml of water were progressively added. The aqueous and organic phases were separated by decantation and the organic phase was washed twice with 300 ml of water and dried over anhydrous calcium sulphate.

By evaporating off the solvent under reduced vacuum and recrystallizing the residue from isopropanol, 26 g of 2-n-butyl-3-[N-(4-methyl-benzenesulfonyl)-4-amino-benzoyl]-benzo [b] thiophene were obtained.

Yield: 60%. M.P.: 128° C.

In another operation, the tin tetrachloride was added at a temperature of 10° C and the yield was 81%.

By the procedure described above and using the appropriate starting product, the following compound was prepared:

| Compound | Melting Point °C. |
|---|---|
| 2-ethyl-3-[N-(4-methyl-benzenesulfonyl)-4-amino-benzoyl]-benzoyl[b] thiophene | 116 (isopropanol) |

(b) Preparation of 2-n-butyl-3-[N-(2-dimethylaminoethyl)-N-(4-methyl-benzenesulfonyl)-4-amino-benzoyl]-benzo [b] thiophene hydrochloride.

Into a 250 ml-flask equipped with a mechanical stirrer and a condenser were introduced 4.3 g (0.0092 mol) of 2-n-butyl-3-[N-(4-methyl-benzenesulfonyl)-4-amino-benzoyl]-benzo [b] thiophene, 3 g (0.023 mol) of potassium carbonate and 100 ml of 1,2-dichloroethane containing 1 ml of water.

While stirring the mixture was refluxed for one hour and 1.45 g (0.01 mol) of 1-chloro-2-dimethylamino-ethane hydrochloride were added. Stirring and refluxing were continued for 3 hours and the solvent was then evaporated off under reduced vacuum.

The residue was taken up in ether and the organic phase was washed three times with water and dried over anhydrous calcium sulphate.

By adding a saturated solution of hydrochloric acid in anhydrous ether the hydrochloride was prepared which was recrystallized from ethyl acetate and 2 g of 2-n-butyl-3-[N-(2-dimethylaminoethyl)-N-(4-methyl-benzene sulfonyl)-4-amino-benzoyl]-benzo [b] thiophene hydrochloride were obtained.

Yield: 37.8%. M.P.: 185° C.

By the procedure described above and using the appropriate starting products, the compounds listed hereunder were prepared:

| Compound | Melting Point °C. |
|---|---|
| 2-ethyl-3-[N-(2-dimethylaminoethyl)-N-(4-methyl-benzenesulfonyl)-4-amino-benzoyl]-benzo [b] thiophene hydrochloride | 238 (ethanol) |
| 2-ethyl-3-[N-(2-diethylaminoethyl)-N-(4-methyl-benzenesulfonyl)-4-amino-benzoyl]-benzo [b] thiophene hydrochloride | 113 (ethyl acetate) |
| 2-ethyl-3-[N-(3-dimethylaminopropyl)-N-(4-methyl-benzenesulfonyl)-4-amino-benzoyl]-benzo [b] thiophene acid oxalate | 156 (methanol) |
| 2-ethyl-3-[N-(3-diethylaminopropyl)-N-(4-methyl-benzenesulfonyl)-4-amino-benzoyl]-benzo [b] thiophene acid oxalate | 96–100 (ethyl acetate) |
| 2-ethyl-3-[N-(3-di-n-propylaminopropyl)-N-(4-methyl-benzenesulfonyl)-4-amino-benzoyl]-benzo [b] thiophene acid oxalate | 124 (ethyl acetate/isopropanol) |
| 2-ethyl-3-[N-(3-di-n-butylaminopropyl)-N-(4-methyl-benzenesulfonyl)-4-amino-benzoyl]-benzo [b] thiophene acid oxalate | 94 (ethyl acetate) |
| 2-n-butyl-3-[N-(2-diethylaminoethyl)-N-(4-methyl-benzenesulfonyl)-4-amino-benzoyl]-benzo [b] thiophene acid oxalate | 162 (ethyl acetate) |
| 2-n-butyl-3-[N-(3-dimethylaminopropyl)-N-(4-methyl-benzenesulfonyl)-4-amino-benzoyl]-benzo [b] thiophene acid oxalate | 90 (ethyl acetate) |
| 2-n-butyl-3-[N-(3-diethylaminopropyl)-N-(4-methyl-benzenesulfonyl)-4-amino-benzoyl]-benzo [b] thiophene acid oxalate | 122 (ethyl acetate) |
| 2-n-butyl-3-[N-(3-di-n-propylaminopropyl)-N-(4-methyl-benzenesulfonyl)-4-amino-benzoyl]-benzo [b] thiophene hydrochloride | 104 (ethyl acetate) |
| 2-n-butyl-3-[N-(3-di-n-butylaminopropyl)-N-(4-methyl-benzenesulfonyl)-4-amino-benzoyl]- | 100 (isopropanol) |

| Compound | Melting Point ° C. |
|---|---|
| -continued | |
| benzo [b] thiophene acid oxalate | |

EXAMPLE 3

2-n-Butyl-3-[N-(2-diethylaminoethyl)-N-(3-pyridylsulfonyl)-4-amino-benzoyl]-benzofuran acid oxalate (a) Preparation of 4-(3-pyridylsulfonamido)-benzoyl chloride Into a 500 ml-flask fitted with a mechanical stirrer and a condenser were introduced 26 g (0.093 mol) of 4-(3-pyridylsulfonamido)-benzoic acid and 180 ml of thionyl chloride, after which a few drops of dimethylformamide were added as catalyst. The mixture was progressively heated to boiling, which was maintained for three hours.

After cooling, petroleum ether (boiling from 40° C to 80° C) was added until precipitation ceased. After filtration, 29.5 g of 4-(3-pyridylsulfonylamido)-benzoyl chloride were obtained.

Yield: 95.2%. M.P.: 170° C.

(b) Preparation of 2-n-butyl-3-[N-(3-pyridylsulfonyl)-4-amino-benzoyl]-benzofuran Into a one-liter flask equipped with a mechanical stirrer, a dropping-funnel and a condenser were introduced 65 g (0.195 mol) of 4-(3-pyridylsulfonamido)-benzoyl chloride, 250 ml (2.5 mols) of tin chloride and 300 ml of dichloroethane. At room-temperature and while stirring 34 g (0.195 mol) of 2-n-butyl-benzofuran were added and stirring was maintained for four and a half hours.

The reaction medium was then poured onto a mixture of hydrochloric acid and ice. Stirring was maintained for 5 hours and the precipitate was filtered out and added to an aqueous solution of sodium bicarbonate. By addition of ether the excess of 4-(3-pyridylsulfonamido)-benzoyl chloride precipitated at the interface of the aqueous and ethereal phases and was filtered out. The ethereal phase was evaporated off and the residue was recrystallized from methanol to give 26.3 g of 2-n-butyl-[N-(3-pyridylsulfonyl)-4-amino-benzoyl]-benzofuran.

Yield: 31%. M.P.: 130° C.

(c) Preparation of 2-n-butyl-3-[N-(2-diethylaminoethyl)-N-(3-pyridylsulfonyl)-4-amino-benzoyl]-benzofuran acid oxalate Into a 250 ml-flask fitted with a mechanical stirrer and a condenser were introduced 6.5 g (0.015 mol) of 2-n-butyl-3-[N-(3-pyridylsulfonyl)-4-amino-benzoyl]-benzofuran, 12 g (0.09 mol) of potassium carbonate and 100 ml of 1,2-dichlorethane.

The mixture was refluxed for one hour while stirring and 2.6 g (0.015 mol) of 1-chloro-2-diethylamino-ethane hydrochloride were then added, and refluxing and stirring were maintained for three hours.

The reaction medium was poured into water and the aqueous and organic phases were separated. The organic phase was dried over anhydrous calcium sulphate and the solvent was evaporated off.

The residue was purified on a silicagel column with acetone as solvent and the pure base was dissolved in anhydrous ether. The oxalate, which was obtained by adding a saturated ethereal solution of oxalic acid, was recrystallized from isopropanol to give 3 g of 2-n-butyl-3-[N-(2-diethylaminoethyl)-N-(3-pyridylsulfonyl)-4-amino-benzoyl]-benzofuran acid oxalate.

Yield: 32%. M.P.: 141°–146° C.

By the procedure described above and using the appropriate starting products, the compounds listed hereunder were prepared:

| Compound | Melting Point ° C. |
|---|---|
| 2-n-butyl-3-[N-(2-dimethylaminoethyl)-N-(3-pyridylsulfonyl)-4-amino-benzoyl]-benzofuran acid oxalate | 169–171 (isopropanol) |
| 2-n-butyl-3-[N-(3-dimethylaminopropyl)-N-(3-pyridylsulfonyl)-4-amino-benzoyl]-benzofuran acid oxalate | 122–124 (ethyl acetate) |
| 2-n-butyl-3-[N-(3-diethylaminopropyl)-N-(3-pyridylsulfonyl)-4-amino-benzoyl]-benzofuran acid oxalate | 77–79 (ethyl acetate) |
| 2-n-butyl-3-[N-(3-di-n-propylaminopropyl)-N-(3-pyridylsulfonyl)-4-amino-benzoyl]-benzofuran acid oxalate | 55–57 (ethyl acetate) |
| 2-n-butyl-3-[N-(3-di-n-butylaminopropyl)-N-(3-pyridylsulfonyl)-4-amino-benzoyl]-benzofuran acid oxalate | 81–84 (purification by chromatography) |

EXAMPLE 4

In accordance with known pharmaceutical techniques, a soft-gelatin capsule containing the following ingredients was prepared:

| Ingredient | mg |
|---|---|
| 2-n-Butyl-3-[N-(2-dimethylaminoethyl)-N-(4-methyl-benzenesulfonyl)-4-amino-benzoyl]-benzofuran hydrochloride | 100 |
| Starches | 99.5 |
| Colloidal silica | 0.5 |
| | 200.0 |

EXAMPLE 5

In accordance with known pharmaceutical techniques, an injectable solution containing the following ingredients was prepared:

| Ingredient | mg |
|---|---|
| 2-n-Butyl-3-[N-(2-dimethylaminoethyl)-N-(4-methyl-benzenesulfonyl)-4-amino-benzoyl]-benzofuran hydrochloride | 150 |
| Polysorbate 80 | 150 |
| Benzyl alcohol | 75 |
| Water | qs. 3 ml |

EXAMPLE 6

In accordance with known pharmaceutical techniques, a suppository, containing the following ingredients was prepared:

| Ingredient | mg |
|---|---|
| 2-n-Butyl-3-[N-(2-dimethylaminoethyl)-N-(4-methyl-benzenesulfonyl)-4-amino-benzoyl]-benzofuran hydrochloride | 100 |
| Mixture of mono- and di-glycerides of saturated acids ($C_{12}$ to $C_{18}$) | 1400 |
| | 1500 |

We claim:

1. A sulfonamide derivative corresponding to the formula:

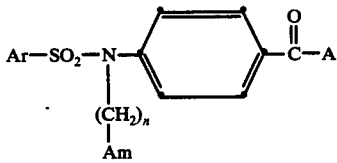

or a pharmaceutically acceptable acid addition salt thereof, wherein Ar represents phenyl, p-chlorophenyl, p-methylphenyl, p-methoxyphenyl, p-nitrophenyl, or pyridyl; Am represents a lower dialkylamino group, piperidino or 2-methyl-piperazino; A represents 3-benzofuryl or 3-benzothienyl substituted in the 2-position by a branched- or straight-chain alkyl group containing from 1 to 4 carbon atoms and optionally substituted in the 5-position by a halogen atom or a lower alkoxy group, and $n$ is the integer 2 or 3.

2. 2-n-Butyl-3-[N-(2-dimethylaminoethyl)-N-(4-methyl-benzenesulfonyl)-4-amino-benzoyl]-benzofuran and pharmaceutically acceptable acid addition salts thereof.

3. 2-n-Butyl-3-[N-(3-di-n-propylaminopropyl)-N-(4-nitro-benzenesulfonyl)-4-amino-benzoyl]-benzofuran and pharmaceutically acceptable acid addition salts thereof.

4. 2-n-Butyl-3-[N-(3-di-n-butylaminopropyl)-N-(4-methoxy-benzenesulfonyl)-4-amino-benzoyl]-benzofuran and pharmaceutically acceptable acid addition salts thereof.

5. 2-n-Propyl-3-[N-(3-di-n-butylaminopropyl)-N-(4-methyl-benzenesulfonyl)-4-amino-benzoyl]-benzofuran and pharmaceutically acceptable acid addition salts thereof.

6. 2-Isopropyl-3-[N-(3-di-n-butylaminopropyl)-N-(4-methyl-benzenesulfonyl)-4-amino-benzoyl]-benzofuran and pharmaceutically acceptable acid addition salts thereof.

7. A pharmaceutical or veterinary composition useful in treating pathological conditions of the heart and particularly angina pectoris, containing an active principle an effective amount of at least one compound of formula I, or a pharmaceutically acceptable acid addition salt thereof, in association with a pharmaceutical excipient or carrier therefor.

8. A pharmaceutical or veterinary composition useful in treating pathological conditions of the heart and particularly angina pectoris, containing as active principle an effective amount of at least one compound selected from the group consisting of:

2-n-butyl-3-[N-(2-dimethylaminoethyl)-N-(4-methyl-benzenesulfonyl)-4-amino-benzoyl]-benzofuran 2-n-butyl-3-[N-(3-di-n-propylaminopropyl)-N-(4-nitro-benzenesulfonyl)-4-amino-benzoyl]-benzofuran 2-n-butyl-3-[N-(3-di-n-butylaminopropyl)-N-(4-methoxy-benzenesulfonyl)-4-amino-benzoyl]-benzofuran 2-n-propyl-3-[N-(3-di-n-butylaminopropyl)-N-(4-methyl-benzenesulfonyl)-4-amino-benzoyl]-benzofuran and 2-isopropyl-3-[N-(3-di-n-butylaminopropyl)-N-(4-methyl-benzenesulfonyl)-4-amino-benzoyl]-benzofuran and the pharmaceutically acceptable acid addition salts thereof in association with a pharmaceutical excipient or carrier therefor.

9. A method of treating pathological conditions of the heart and particularly angina pectoris in a subject in need of such treatment which method comprises administering to said subject an effective dose of at least one compound of formula I, or a pharmaceutically acceptable acid addition salt thereof.

10. A method of treating pathological conditions of the heart and particularly angina pectoris in a subject in need of such treatment which method comprises administering to said subject an effective dose of at least one compound selected from the group consisting of:

2-n-butyl-3-[N-(2-dimethylaminoethyl)-N-(4-methyl-benzenesulfonyl)-4-amino-benzoyl]-benzofuran 2-n-butyl-3-[N-(3-di-n-propylaminopropyl)-N-(4-nitro-benzenesulfonyl)-4-amino-benzoyl]-benzofuran 2-n-butyl-3-[N-(3-di-n-butylaminopropyl)-N-(4-methoxy-benzenesulfonyl)-4-amino-benzoyl]-benzofuran 2-n-propyl-3-[N-(3-di-n-butylaminopropyl)-N-(4-methyl-benzenesulfonyl)-4-amino-benzoyl]-benzofuran and 2-isopropyl-3-[N-(3-di-n-butylaminopropyl)-N-(4-methyl-benzenesulfonyl)-4-amino-benzoyl]-benzofuran and the pharmaceutically acceptable acid addition salts thereof.

* * * * *